(12) United States Patent
Wheeler (10) Patent No.: US 9,618,375 B2
(45) Date of Patent: *Apr. 11, 2017

(54) DENSITY OR SPECIFIC GRAVITY METER IN ELECTRICAL COMMUNICATION WITH A VOLUMETRIC FLOW METER AND BOTH IN ELECTRICAL COMMUNICATION WITH A METER ELECTRONICS THAT OUTPUTS A MASS FLOW MEASUREMENT

(71) Applicant: Micro Motion, Inc., Boulder, CO (US)

(72) Inventor: Simon P. H. Wheeler, Erie, CO (US)

(73) Assignee: Micro Motion, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/785,540

(22) PCT Filed: Apr. 30, 2013

(86) PCT No.: PCT/US2013/038732
§ 371 (c)(1),
(2) Date: Oct. 19, 2015

(87) PCT Pub. No.: WO2014/178828
PCT Pub. Date: Nov. 6, 2014

(65) Prior Publication Data
US 2016/0084691 A1    Mar. 24, 2016

(51) Int. Cl.
*G01F 1/86*    (2006.01)
*G01F 1/84*    (2006.01)
(Continued)

(52) U.S. Cl.
CPC ............ *G01F 1/849* (2013.01); *G01F 1/00* (2013.01); *G01F 15/063* (2013.01); *G01N 9/36* (2013.01)

(58) Field of Classification Search
None
See application file for complete search history.

(56) References Cited

U.S. PATENT DOCUMENTS 3,739,635 A    6/1973    Stuart
4,589,279 A    5/1986    Mitsuyasu et al.
(Continued)

FOREIGN PATENT DOCUMENTS

GB    2483369 A    3/2012
JP    8-201130 A    8/1996
(Continued)

*Primary Examiner* — Harshad R Patel
(74) *Attorney, Agent, or Firm* — The Ollila Law Group LLC (57) ABSTRACT

A flow rate sensor system (200) is provided. The flow rate sensor system (200) includes a density or specific gravity meter (202) including a sensor assembly (204a) and a density or specific gravity meter electronics (204b) configured to generate a density or specific gravity measurement of a process fluid. The flow rate sensor system (200) further includes a mass flow meter (203) including a sensor assembly (205a) and a mass flow meter electronics (205b) configured to generate a mass flow rate of the process fluid and in electrical communication with the density or specific gravity meter electronics (204b). A remote processing system (207) is provided that is in electrical communication with only one of the density or specific gravity meter electronics (204b) or the mass flow meter electronics (205b). The remote processing system (207) is configured to receive a volume or energy flow measurement of the process fluid generated by the density or specific gravity meter electronics (204b) or the volumetric meter electronics (205b) based on the generated density or specific gravity measurement and the generated mass flow rate.

10 Claims, 4 Drawing Sheets

(51) Int. Cl.
*G01F 1/00* (2006.01)
*G01F 15/06* (2006.01)
*G01N 9/36* (2006.01)

(56) References Cited

U.S. PATENT DOCUMENTS

| | | | |
|---|---|---|---|
| 5,687,100 | A | 11/1997 | Buttler et al. |
| 9,470,568 | B2 * | 10/2016 | Patten .................. G01F 1/86 |
| 2005/0034535 | A1 | 2/2005 | Sprague |
| 2005/0061061 | A1 | 3/2005 | Stephenson |
| 2011/0247432 | A1 | 10/2011 | Kelnhofer et al. |

FOREIGN PATENT DOCUMENTS

| | | |
|---|---|---|
| JP | 10-90028 A | 4/1998 |
| JP | 2007-263777 A | 10/2007 |
| WO | 03021204 A1 | 3/2003 |

* cited by examiner

DENSITY OR SPECIFIC GRAVITY METER IN ELECTRICAL COMMUNICATION WITH A VOLUMETRIC FLOW METER AND BOTH IN ELECTRICAL COMMUNICATION WITH A METER ELECTRONICS THAT OUTPUTS A MASS FLOW MEASUREMENT

TECHNICAL FIELD

The embodiments described below relate to, combination flow sensor systems, and more particularly, to a density/specific gravity meter in electrical communication with a mass flow meter that outputs a mass, volume or energy flow measurements.

BACKGROUND OF THE INVENTION

Mass flow meters can measure a mass flow rate of a fluid directly and a volume flow rate. For instance, when determining volume, a density and mass meter must use the following equation:

$$\dot{m} = Q * \rho \qquad (1)$$

Where:
$\dot{m}$ is the mass flow rate;
Q is the volumetric flow rate; and
$\rho$ is the density.

However, in cases where a highly accurate volume flow measurement or energy flow is needed, a user must install a density meter or specific gravity meter in combination with the mass flow meter.

Figure 1:
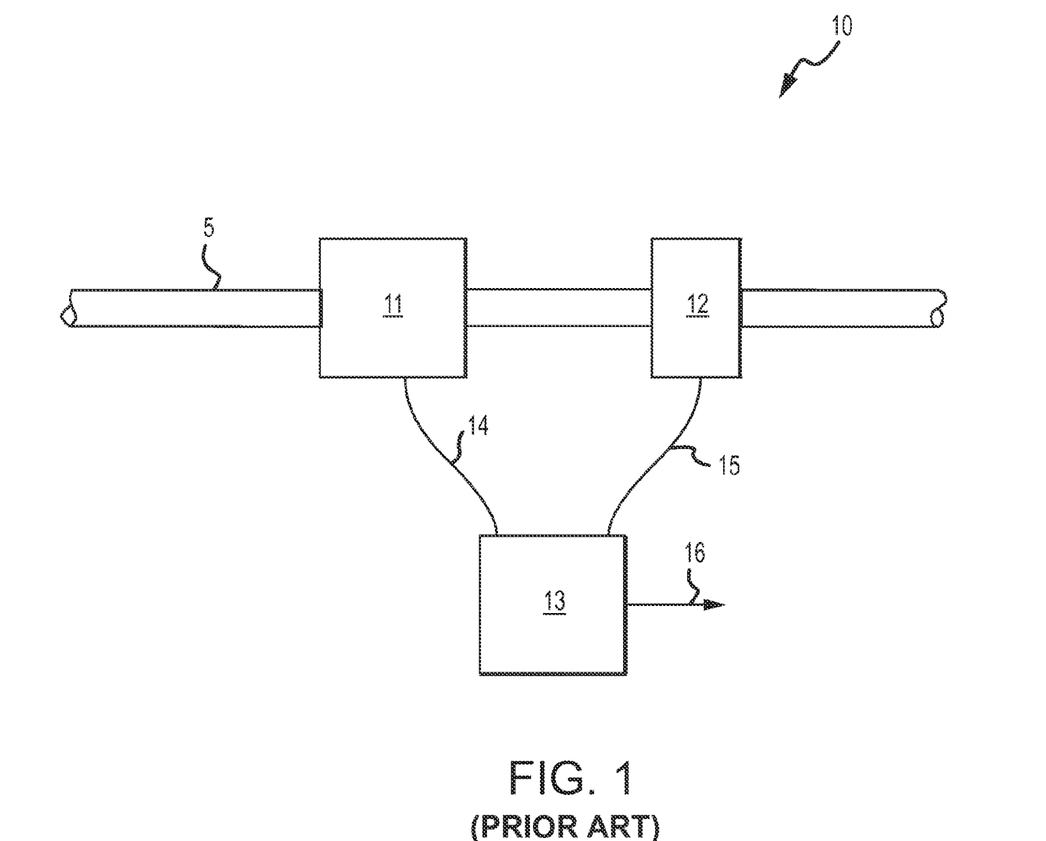
FIG. 1 shows a prior art flow rate system.

One problem with the combination of a density or specific gravity meter and a mass flow meter is in order to generate a highly accurate volume flow rate or energy flow output an excessive amount of wiring is involved as shown in FIG. 1.

FIG. 1 shows a prior art flow sensor system 10. The prior art flow sensor system 10 can include a density meter 11 and a mass flow meter 12. The density meter 11 and the mass flow meter 12 are positioned within a flow conduit 5 carrying a process fluid. The density meter 11 may comprise any one of well-known density meters, such as a vibrating element density meter, a hygrometer, an x-ray densitometer, a gamma densitometer, etc. The mass flow meter 12 may comprise any well-known meter that measures a mass flow rate, such as Coriolis meter, thermal mass meter, etc. In the above example and throughout this application the density meter may be substituted with a specific gravity(SG) meter so that energy flow output can be obtained.

The prior art flow sensor system 10 also includes a central processing system 13. As shown, the density meter 11 is in electrical communication with the central processing system 13 via electrical leads 14. Similarly, the mass flow meter 12 is in electrical communication with the central processing system 13 via electrical leads 15. Therefore, each of the meters 11, 12 sends signals to the central processing system 13. The central processing system 13 processes the signals received from the density meter 11 to generate a density measurement. Likewise, the central processing system 13 processes the signals received from the mass flow meter 12 to generate a mass flow rate. The central processing system 13 may subsequently generate a volume flow rate based on the generated density and mass flow rate. The volume flow rate may then be provided to a user or another processing system via leads 16. As an alternative, the central processing system 13 may simply output the individual density and the mass flow rate without calculating a volume flow rate. The customer must then use another processing system to determine the volume flow rate based on the output from the central processing system 13.

The prior art flow system 10 suffers from a number of problems. One problem is due to the increased amount of wiring or signal paths required. While the density meter 11 and the mass flow meter 12 are often located relatively close to one another, the central processing system 13 may be located remotely from the density meter 11 and the mass flow meter 12. Consequently, because each meter 11 and 12 communicates with the central processing system 13 independently, the amount of wiring or number of signal paths is duplicative.

Another problem with the prior art system 10 is that if either the density meter 11 or the mass flow meter 12 needs to be replaced, the central processing system 13 needs to be reprogrammed to receive the new signals from the new meter. Often, the central processing system 13 may be a customer's own equipment and thus, the customer is required to perform the updated programming.

Similarly, many users simply want the volumetric flow rate and do not necessarily need to know the particular density or the mass flow rate. However, in the prior art system 10, the user is only provided signals indicating the density and the mass flow rate and is required to perform the calculation of the volume flow rate independently.

Therefore, there is a need in the art for a system that can provide a volume or energy flow output using a density/SG meter and a mass flow rate meter. Further, there is a need in the art for a system that can reduce or eliminate the required signal paths or wiring, especially between the meters and a central processing system. The embodiments described below overcome these and other problems and an advance in the art is achieved. The embodiments described below provide a volume flow rate system that uses one or both of the density/SG meter and the mass flow rate meter to perform the volume or energy flow calculation. Consequently, only one of the meters needs to be in communication with a central processing system, resulting in a reduction in the number of signal paths and/or reduced wiring. Therefore, the system outputs a volume flow rate and the signal paths and/or wiring required to communicate with the central processing system is reduced or eliminated.

SUMMARY OF THE INVENTION

A combination flow rate sensor system is provided according to an embodiment. The flow rate sensor system comprises a density meter including a sensor assembly and a density meter electronics configured to generate a density measurement of a process fluid. According to an embodiment, the flow rate sensor system further comprises a mass flow meter including a sensor assembly and a mass flow meter electronics configured to generate a mass flow rate of the process fluid and in electrical communication with the meter electronics of the density meter. According to an embodiment, the flow rate sensor system further comprises a remote processing system in electrical communication with only one of the density meter electronics or the mass flow meter electronics. The remote processing system is configured to receive measurements of the process fluid generated by the density or specific gravity meter electronics or the mass meter electronics based on the generated density or specific gravity measurement and the generated mass flow rate.

A method for generating a flow rate measurement of a process fluid in a fluid conduit is provided according to an embodiment. The method comprises a step of determining a density or specific gravity of the process fluid with a density or specific gravity meter including a sensor assembly in fluid communication with the process fluid and density meter electronics. According to an embodiment, the method further comprises a step of determining a mass flow rate of the process fluid with a mass flow meter including a sensor assembly in fluid communication with the process fluid and mass flow meter electronics. According to an embodiment, electrical communication is provided between the density meter electronics and the mass flow meter electronics. The method further comprises a step of using at least one of the density or specific gravity meter electronics or the mass flow meter electronics to determine a volume or energy flow of the process fluid based on the determined density or specific gravity and the determined mass flow rate. The method further comprises a step of providing the volume or energy flow to a remote processing system in electrical communication with only one of the density meter electronics or the mass flow meter electronics.

ASPECTS

According to an aspect, a flow rate sensor system comprises:
a density or specific gravity meter including a sensor assembly and a density or specific gravity meter electronics configured to generate a density or specific gravity measurement of a process fluid;
a mass flow meter including a sensor assembly and a mass flow meter electronics configured to generate a mass flow rate of the process fluid and in electrical communication with the density or specific gravity meter electronics; and
a remote processing system in electrical communication with only one of the density or specific gravity meter electronics or the mass meter electronics and configured to receive a volume or energy flow output measurement of the process fluid generated by the density or specific gravity meter electronics or the mass flow meter electronics based on the generated density or specific gravity measurement and the generated mass flow rate.

Preferably, the sensor assembly of the density or specific gravity meter and the sensor assembly of the mass flow meter are located in line with a fluid conduit carrying the process fluid.

Preferably, the sensor assembly of the mass flow meter is located in line with a fluid conduit carrying the process fluid and the sensor assembly of the density or specific gravity meter is located in a slip stream coupled to the fluid conduit to receive a portion of the process fluid.

Preferably, the density or specific gravity measurement and the mass flow rate are generated substantially simultaneously.

Preferably, the density or specific gravity measurement comprises an average density or specific gravity.

According to another aspect, a method for generating a volume or energy flow output measurement of a process fluid in a fluid conduit comprises steps of:
determining a density or specific gravity of the process fluid with a density or specific gravity meter including a sensor assembly in fluid communication with the process fluid and a density or specific gravity meter electronics;
determining a mass flow rate of the process fluid with a mass flow meter including a sensor assembly in fluid communication with the process fluid and a mass flow meter electronics;
providing electrical communication between the density or specific gravity meter electronics and the mass flow meter electronics;
using at least one of the density or specific gravity meter electronics or the mass flow meter electronics to determine a volume or energy flow measurement of the process fluid based on the determined density or specific gravity and the determined mass flow rate; and
providing the volume or energy flow measurement to a remote processing system in electrical communication with only one of the density or specific gravity meter electronics or the mass meter electronics.

Preferably, the sensor assembly of the density or specific gravity meter and the sensor assembly of the mass flow meter are located in line with the fluid conduit carrying the process fluid.

Preferably, the sensor assembly of the mass flow meter is located in line with the fluid conduit carrying the process fluid and the sensor assembly of the density or specific gravity meter is located in a slip stream coupled to the fluid conduit to receive a portion of the process fluid.

Preferably, the density or specific gravity measurement and the mass flow rate are determined substantially simultaneously.

Preferably, the density or specific gravity measurement comprises an average density or specific gravity.

DETAILED DESCRIPTION OF THE INVENTION

Figure 2:
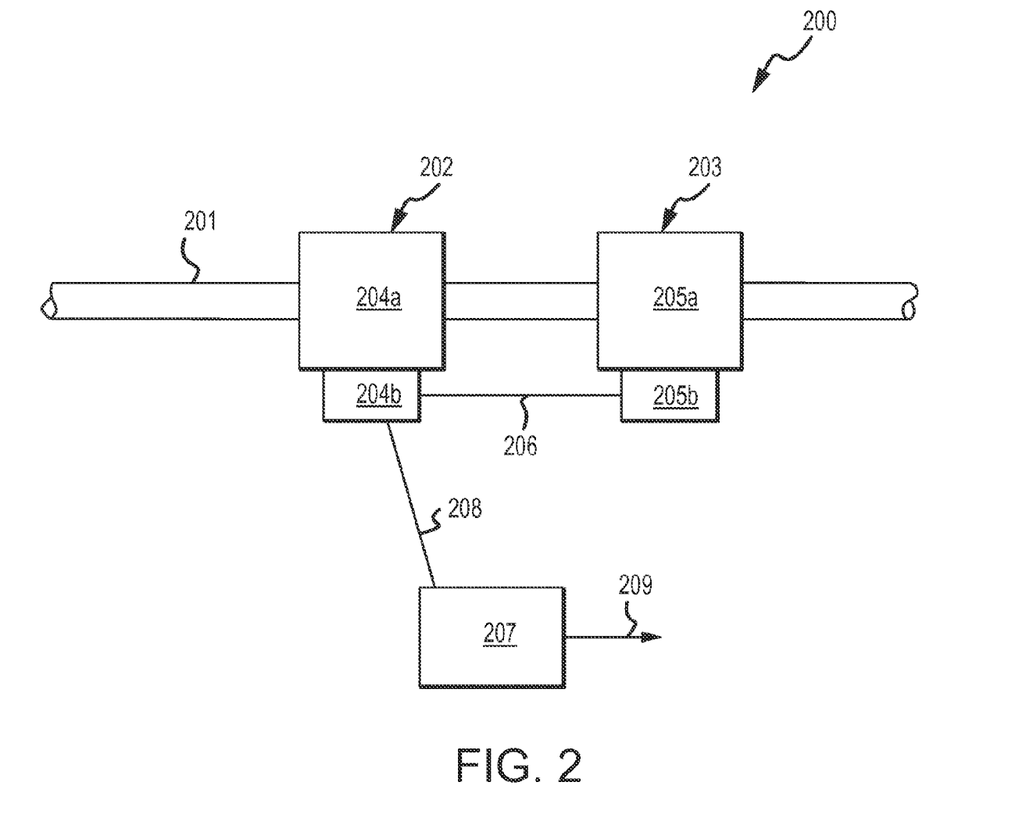
FIG. 2 shows a flow rate sensor system according to an embodiment.
Figure 3:
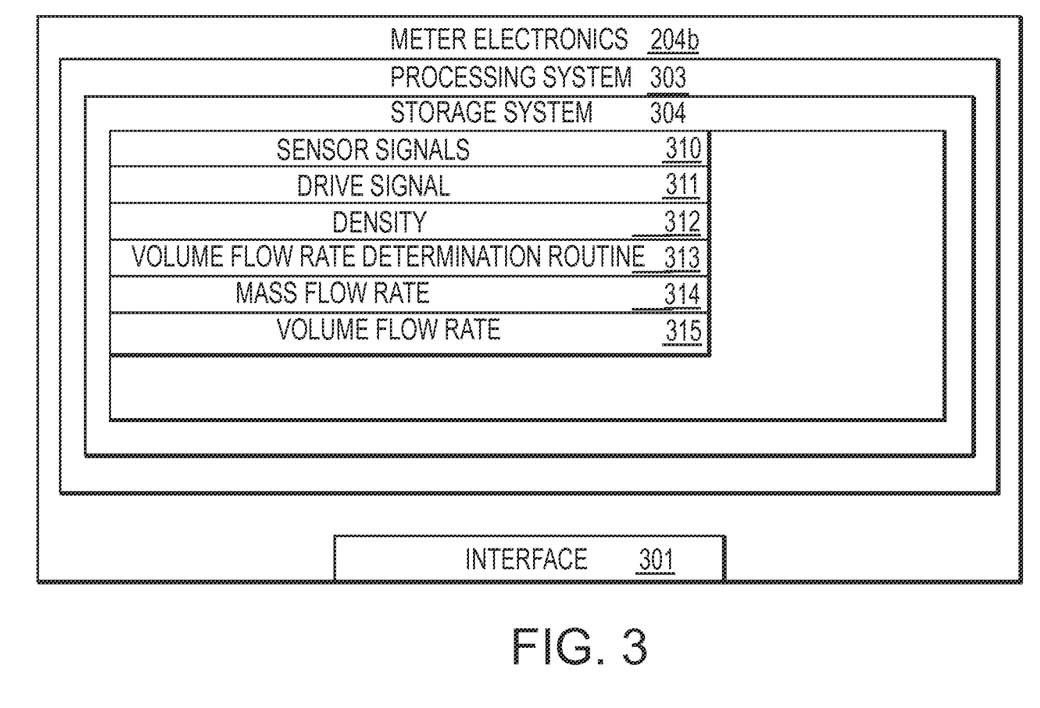
FIG. 3 shows meter electronics according to an embodiment.
Figure 4:
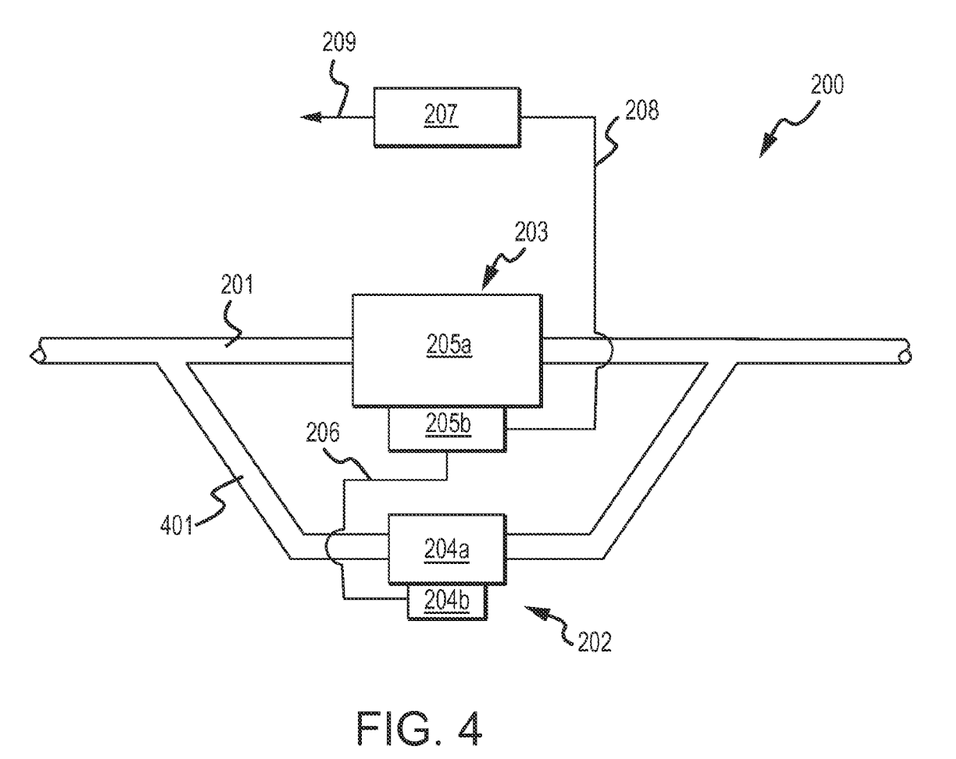
FIG. 4 shows the flow rate sensor system according to another embodiment.

FIGS. 2-4 and the following description depict specific examples to teach those skilled in the art how to make and use the best mode of embodiments of a flow sensor system. For the purpose of teaching inventive principles, some conventional aspects have been simplified or omitted. Those skilled in the art will appreciate variations from these examples that fall within the scope of the present description. For example, a specific gravity meter may be substituted for a density meter in combination with a mass flow sensor in order to generate energy output measurements. Those skilled in the art will appreciate that the features described below can be combined in various ways to form multiple variations of the mass flow rate system. As a result, the embodiments described below are not limited to the specific examples described below, but only by the claims and their equivalents.

FIG. 2 shows a flow sensor system 200 according to an embodiment. According to an embodiment, the flow sensor system 200 can be positioned within a flow conduit 201 receiving a process fluid or some other type of flow stream. The flow sensor system 200 can include a density meter 202 and a mass flow meter 203. The density meter 202 may comprise any well-known density meters, such as a vibrating element density meter, a hygrometer, an x-ray densitometer, a gamma densitometer, etc. The particular type of density meter may depend upon the particular application and should in no way limit the scope of the present embodiment. The mass flow meter 203 may comprise any well-known meter that measures a mass flow rate, such as Coriolis flow meter, thermal mass meter, etc. According to an embodiment, the density meter 202 and the mass flow meter 203 can be placed in series in line with the conduit 201. In the embodiment shown, the density meter 202 is positioned upstream from the mass flow meter 203; however, in other embodiments, the order can be reversed. In alternative embodiments, the density meter 202 can be placed in a slip stream, which branches off from the conduit 201 (See FIG. 4).

According to an embodiment, the density meter 202 comprises a sensor assembly 204a, which receives the flowing fluid. The density meter 202 further comprises density meter electronics 204b. Although the density meter electronics 204b is shown as being physically coupled to the sensor assembly 204a, in other embodiments, the two components may simply be electrically coupled via an electrical lead or wirelessly coupled. In either situation, the sensor assembly 204a is in electrical communication with the density meter electronics 204b via an electrical lead or wirelessly using any known wireless protocol including Bluetooth, HART or Rosemount THUM technology (not shown).

According to an embodiment, the density meter electronics 204b can receive sensor signals from the sensor assembly 204a. The density meter electronics 204b can process the received sensor signals to generate a measured density of the fluid flowing through the conduit 201 as is generally known in the art.

According to an embodiment, the mass flow meter 203 comprises a sensor assembly 205a, which receives the process fluid in the fluid conduit 201. The mass flow meter 203 further comprises a mass flow meter electronics 205b. In a manner similar to the density meter 202, while the mass flow meter electronics 205b is shown physically coupled to the sensor assembly 205a, in other embodiments, the two components may simply be coupled via an electrical lead. In either situation, the sensor assembly 205a is in electrical communication with the mass flow meter electronics 205b via an electrical lead (not shown).

According to an embodiment, the mass flow meter electronics 205b can receive signals from the sensor assembly 205a. The mass flow meter electronics 205b can process the signals and generate a mass flow rate as is generally known in the art.

According to an embodiment, the two meter electronics 204b, 205b are in electrical communication with one another via the electrical lead 206. The electrical communication between the two meter electronics 204b, 205b allows the generated measurement from one of the meter electronics to be communicated to the other meter electronics. For example, in the configuration shown, the density meter electronics 204b can receive the generated mass flow rate from the mass flow meter electronics 205b. With the mass flow rate received from the mass flow meter 203 along with the generated density, the density meter 202 can generate a volume flow rate using equation (1). According to an embodiment, the generated volume flow rate can then be output to a remote processing system 207 via electrical lead 208. According to an embodiment, the electrical lead 208 can additionally provide power to the density meter 202 and the mass flow meter 203. In some embodiments, the remote processing system 207 may include a further output lead 209. The output lead 209 can provide communication with a further processing system, for example.

According to an embodiment, the remote processing system 207 may be located at a distance greater than the distance between the density meter 202 and the mass flow meter 203. However, according to another embodiment, the remote processing system 207 may be located in close proximity to the two meters 202, 203. For example, the remote processing system 207 may be located at the same distance or a shorter distance than the distance between the density meter 202 and the mass flow meter 203. The particular location of the remote processing system 207 with respect to the meters 202, 203 should in no way limit the scope of the present embodiment and will depend upon the particular application.

The remote processing system 207 can comprise a general-purpose computer, a micro-processing system, a logic circuit, or some other general purpose or customized processing device. The remote processing system 207 can be distributed among multiple processing devices. The remote processing system 207 can include any manner of integral or independent electronic storage medium.

As can be appreciated, only one of the density meter 202 or the mass flow meter 203 is in direct electrical communication with the remote processing system 207. Although in the embodiment shown in FIG. 2, the density meter 202 is in direct electrical communication with the remote processing system 207, in other embodiments, the mass flow meter 203 can be in direct electrical communication with the remote processing system 207 instead. In either situation, the amount of wiring required is substantially reduced compared to the prior art system shown in FIG. 1. Additionally, the meter electronics that is electrically coupled with the remote processing system 207, outputs a volume flow rate. Therefore, the remote processing system 207 does not have to be specially configured to calculate a volume flow rate from a density and a mass flow rate.

FIG. 3 shows the density meter electronics 204b according to an embodiment of the invention. It should be appreciated that many of the features of the density meter electronics 204b can also be found in the mass flow meter electronics 205b of the mass flow meter 203. However, a description of the mass flow meter electronics 205b is omitted for brevity of the description. The density meter electronics 204b can include an interface 301 and a processing system 303. The processing system 303 may include a storage system 304. The storage system 304 may comprise an internal memory as shown, or alternatively, may comprise an external memory. The density meter electronics 204b can generate a drive signal 311 and supply the drive signal 311 to a driver (not shown) of the sensor assembly 204a. The density meter electronics 204b can also receive sensor signals 310 from the sensor assembly 204a. The density meter electronics 204b can process the sensor signals 310 in order to obtain a density 312 of the material flowing through the conduit 201. The density 312 can be stored for later use.

In addition to the sensor signals 310 received from the sensor assembly 204a, the interface 301 can also receive a generated mass flow rate 314 from the mass flow meter electronics 205b. The interface 301 may perform any necessary or desired signal conditioning, such as any manner of formatting, amplification, buffering, etc. Alternatively, some or all of the signal conditioning can be performed in the processing system 303. In addition, the interface 301 can enable communications between the density meter electronics 204b and the remote processing system 207. The interface 301 can be capable of any manner of electronic, optical, or wireless communication.

The interface 301 in one embodiment can include a digitizer (not shown); wherein the sensor signals 310 comprise analog sensor signals. The digitizer can sample and digitize the analog sensor signals and produce digital sensor signals. The digitizer can also perform any needed decimation, wherein the digital sensor signal is decimated in order to reduce the amount of signal processing needed and to reduce the processing time.

The processing system 303 can conduct operations of the density meter electronics 204b. The processing system 303 can execute the data processing required to implement one or more processing routines, such as the volume flow rate determination routine 313. The volume flow determination routine 313 can use equation (1) along with the generated density 312 and the received mass flow rate 314 to generate a volume flow rate 315. As discussed above, the volume flow rate 315 can then be output to the external remote processing system 207. In some embodiments, the processing system 300 may additionally output the density 312 and/or the mass flow rate 314.

It should be understood that the meter electronics 220 may include various other components and functions that are generally known in the art. These additional features are omitted from the description and the figures for the purpose of brevity. Therefore, the present invention should not be limited to the specific embodiments shown and discussed.

FIG. 4 shows the flow sensor system 200 according to another embodiment. In the embodiment shown in FIG. 4, the sensor assembly 204a of the density meter 202 is located within a slip stream 401, which branches off from the main conduit 201. The slip stream 401 is generally smaller than the conduit 201 such that only a small amount of the fluid flows into the slip stream 401. Although the mass flow meter 203 is positioned between the first and second ends of the slip stream 401 in the embodiment shown in FIG. 4, the mass flow meter 203 could be positioned at other areas of the conduit 201. For example, in some embodiments, the mass flow meter 203 is positioned just outside the ends of the slip stream 401 such that all of the fluid flows through the mass flow meter 203 rather than a portion of the fluid bypassing the mass flow meter 203. Therefore, a correction does not have to be performed to account for the amount of fluid bypassing the mass flow meter 203. However, in many embodiments, the mass flow meter 203 will be positioned close to the slip stream 401 so that the mass flow meter 203 and the density meter 202 are measuring substantially the same fluid at any given time.

According to the embodiment shown in FIG. 4, the sensor assembly 204a can receive a small portion of the fluid flowing through the system 200. This may be advantageous in some embodiments as the sensor assembly 204a can be made substantially smaller than in the embodiment shown in FIG. 2 as a smaller flow rate is being received by the density meter 202 in FIG. 4. Therefore, if the density meter 202 is formed from high cost materials, such as a tube made from titanium or tantalum, the cost of the sensor assembly 204a can be reduced due to the reduced size.

According to the embodiment shown in FIG. 4, the two meter electronics 204b, 205b are still in electrical communication with one another so that only one of the meter electronics 205a or 205b needs to be in direct electrical communication with the remote processing system 207. In the embodiment shown in FIG. 4, the mass flow meter electronics 205b is in direct electrical communication with the remote processing system 207 rather than the density meter 202. As can be appreciated, in this embodiment, the mass flow meter electronics 205b will be configured to receive the density measurement from the density meter electronics 204b and generate the volume flow rate based on the received density 312 and the mass flow rate 314.

In use, the flow rate sensor system 200 may be used to generate a volume flow rate based on individually determined mass flow rates and densities generated from two separate sensor assemblies 204a, 205a. According to an embodiment, the density meter 202 can generate a density measurement 312, as the process fluid flows through the conduit 201. According to an embodiment, substantially simultaneously, the mass flow meter 203 can generate a mass flow rate 314. According to another embodiment, the density meter 202 may generate an average density measurement. For example, the meter electronics 204a may store and keep a rolling average density determined from previous density measurements. The previous density measurements may be based on a predetermined number of previously received sensor signals 310, for example.

According to an embodiment, at least one of the meter electronics 204b, 205b can receive the fluid measurement from the other meter electronics. For example, in the embodiment shown in FIG. 2, the density meter electronics 204b can receive the mass flow rate 314 from the mass flow meter electronics 205b. Conversely, in the embodiment shown in FIG. 3, the mass flow meter electronics 205b can receive the density measurement 312 from the density meter electronics 204b. Preferably, the meter electronics that receives the fluid measurement is the meter electronics that is in direct electrical communication with the remote processing system 207. However, the present embodiment should not be so limited. For example, in FIG. 2, the density meter 202 is in direct electrical communication with the remote processing system 207. In some embodiments, the mass flow meter electronics 205b may receive the density measurement from the density meter 202. In yet another embodiment, each of the meter electronics 204b, 205b may send the generated measurement to the other meter electronics such that each of the meter electronics 204b, 205b includes both a density measurement and a mass flow rate measurement.

According to an embodiment, once one of the meter electronics includes both the density measurement 312 and the mass flow rate 314, the meter electronics can process the two measurements to generate a volume flow rate 315. The generated volume flow rate 315 can then be sent to the remote processing system 207 via the lead 208. If the meter electronics that generates the volume flow rate is not in direct electrical communication with the remote processing system 207, the generated volume flow rate can be sent to the meter electronics that is in direct electrical communication with the remote processing system 207 and subsequently pass the volume flow rate 315 on to the remote processing system 207.

Therefore, as can be appreciated, the remote processing system 207 can receive a volume flow rate from a combination density meter 202 and mass flow meter 203 without having to separately perform the volume flow rate calculation. This advantageously simplifies the processing required of the remote processing system 207 as well as substantially reduces the amount of wiring required. Additionally, if either of the meters 202, 203 need to be replaced, the remote processing system 207 does not have to be reconfigured.

According to an embodiment, if both of the meter electronics 204b, 205b includes the density measurement and the mass flow rate measurement, both of the meter electronics 204b, 205b may generate a volume flow rate measurement. This allows either of the meter electronics 204b, 205b to send the volume flow rate measurement to the remote processing system 207. Further, in the event that one of the meters 202, 203 need to be replaced, the remaining meter can easily provide the volume flow measurement to the remote processing system 207.

The detailed descriptions of the above embodiments are not exhaustive descriptions of all embodiments contemplated by the inventors to be within the scope of the present description. Indeed, persons skilled in the art will recognize that certain elements of the above-described embodiments may variously be combined or eliminated to create further embodiments, and such further embodiments fall within the scope and teachings of the present description. It will also be apparent to those of ordinary skill in the art that the above-described embodiments may be combined in whole or in part to create additional embodiments within the scope and teachings of the present description.

Thus, although specific embodiments are described herein for illustrative purposes, various equivalent modifications are possible within the scope of the present description, as those skilled in the relevant art will recognize. The teachings provided herein can be applied to other mass flow systems, and not just to the embodiments described above and shown in the accompanying figures. Accordingly, the scope of the embodiments described above should be determined from the following claims.

I claim:

1. A flow rate sensor system (200), comprising:
    a density or specific gravity meter (202) including a sensor assembly (204a) and a density or specific gravity meter electronics (204b) configured to generate a density or specific gravity measurement of a process fluid;
    a mass flow meter (203) including a sensor assembly (205a) and a mass flow meter electronics (205b) configured to generate a mass flow rate of the process fluid and in electrical communication with the density or specific gravity meter electronics (204b); and
    a remote processing system (207) in electrical communication with only one of the density or specific gravity meter electronics (204b) or the mass flow meter electronics (205b) and configured to receive measurements of the process fluid generated by the density or specific gravity meter electronics (204b) or the mass flow meter electronics (205b) based on the generated density or specific gravity measurement and the mass flow rate.

2. The flow rate sensor system (200) of claim 1, wherein the sensor assembly (204a) of the density or specific gravity meter (202) and the sensor assembly (205a) of the mass flow meter (203) are located in line with a fluid conduit (201) carrying the process fluid.

3. The flow rate sensor system (200) of claim 1, wherein the sensor assembly (205a) of the mass flow meter (203) is located in line with a fluid conduit (201) carrying the process fluid and the sensor assembly (204a) of the density or specific gravity meter (202) is located in a slip stream (401) coupled to the fluid conduit (201) to receive a portion of the process fluid.

4. The flow rate sensor system (200) of claim 1, wherein the density or specific gravity measurement and the mass flow rate are generated substantially simultaneously.

5. The flow rate sensor system (200) of claim 1, wherein the density or specific gravity measurement comprises an average density or specific gravity.

6. A method for generating a flow rate measurement of a process fluid in a fluid conduit, comprising steps of:
    determining a density or specific gravity of the process fluid with a density or specific gravity meter including a sensor assembly in fluid communication with the process fluid and a density or specific gravity meter electronics;
    determining a mass flow rate of the process fluid with a mass flow meter including a sensor assembly in fluid communication with the process fluid and a mass flow meter electronics;
    providing electrical communication between the density or specific gravity meter electronics and the mass flow meter electronics;
    using at least one of the density or specific gravity meter electronics or the mass flow meter electronics to determine a volume or energy flow of the process fluid based on the determined density or specific gravity and the determined mass flow rate; and
    providing the volume or energy flow to a remote processing system in electrical communication with only one of the density or specific gravity meter electronics or the mass meter electronics.

7. The method of claim 6, wherein the sensor assembly of the density or specific gravity meter and the sensor assembly of the mass flow meter are located in line with the fluid conduit carrying the process fluid.

8. The method of claim 6, wherein the sensor assembly of the mass flow meter is located in line with the fluid conduit carrying the process fluid and the sensor assembly of the density or specific gravity meter is located in a slip stream coupled to the fluid conduit to receive a portion of the process fluid.

9. The method of claim 6, wherein the density or specific gravity measurement and the mass flow rate are determined substantially simultaneously.

10. The method of claim 6, wherein the density or specific gravity measurement comprises an average density or specific gravity.

* * * * *